United States Patent [19]
Meisel et al.

[11] Patent Number: 5,914,425
[45] Date of Patent: Jun. 22, 1999

[54] MODIFICATIONS OF 2-AMINO-4-(4-5FLUOROBENZYLAMINO)-1-ETHOXYCARBONYLAMINOBENZENE, AND PROCESSES FOR THEIR PREPARATION

[75] Inventors: Peter Meisel; Karl-Friedrich Landgraf, both of Dresden; Jürgen Schäfer, Radebeul; Wilfried Thiel, Langebüuch; Matthias Rischer, Maintal; Alfred Olbrich, Halle/Westf.; Bernhard Kutscher, Maintal, all of Germany

[73] Assignee: ASTA Medica Aktiengesellschaft, Dresden, Germany

[21] Appl. No.: 09/004,926

[22] Filed: Jan. 9, 1998

[30] Foreign Application Priority Data

Jan. 20, 1997 [DE] Germany .............................. 197 01 694

[51] Int. Cl.⁶ .................................................. C07C 261/00
[52] U.S. Cl. .............................................................. 560/27
[58] Field of Search ................................................. 560/27

[56] References Cited

U.S. PATENT DOCUMENTS 5,384,330  1/1995  Dieter et al. .

*Primary Examiner*—Brian M. Burn
*Assistant Examiner*—Brian J. Davis
*Attorney, Agent, or Firm*—Pillsbury Madison & Sutro LLP

[57] ABSTRACT

The invention relates to novel modifications of the compound 2-amino-4-(4-fluorobenzylamino)-1-ethoxycarbonylaminobenzene of the formula I

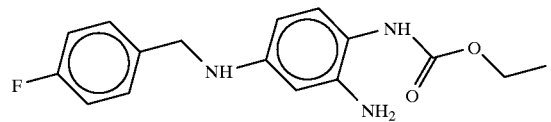

processes for their preparation and their use in pharmaceutical compositions.

12 Claims, 5 Drawing Sheets

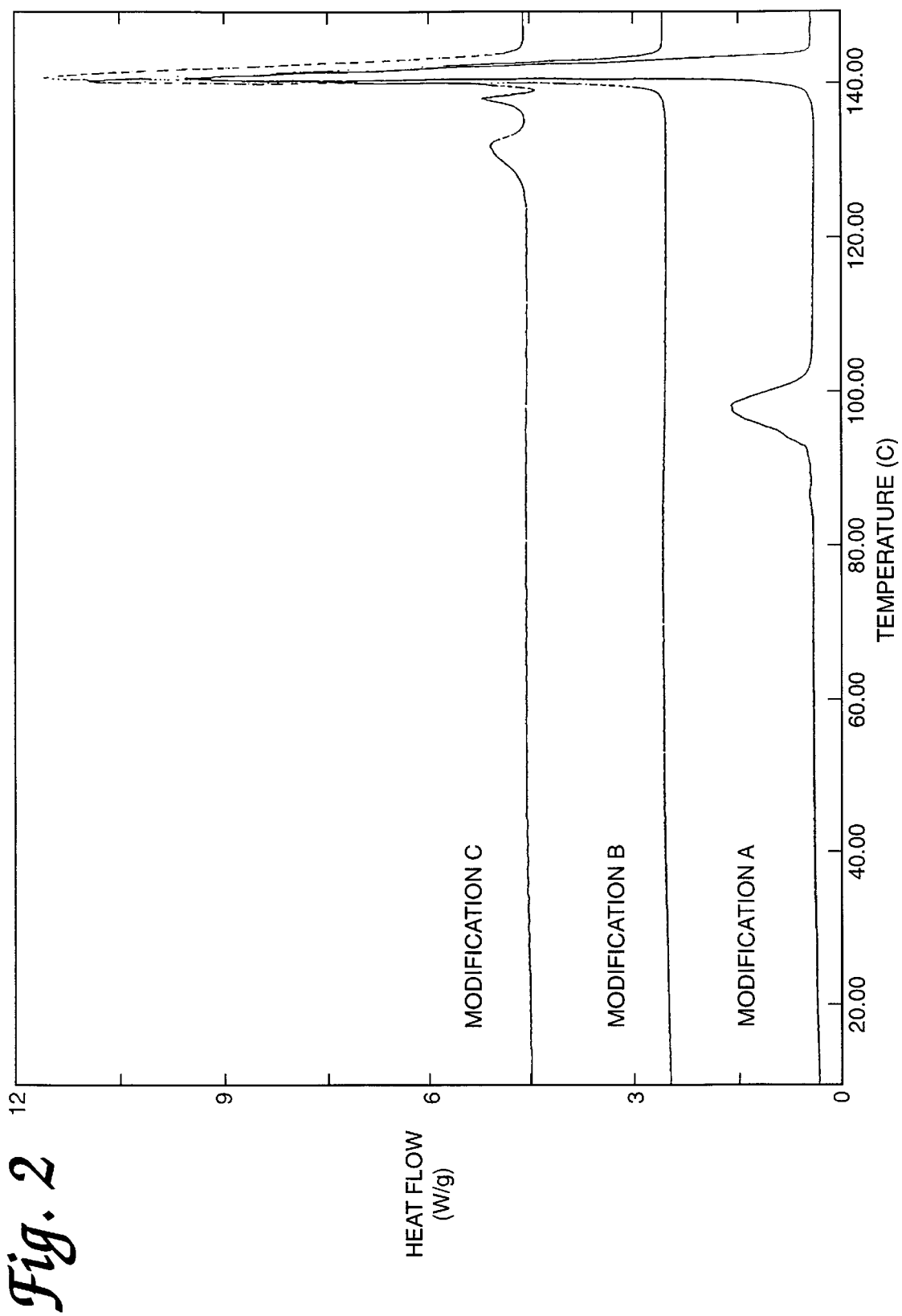

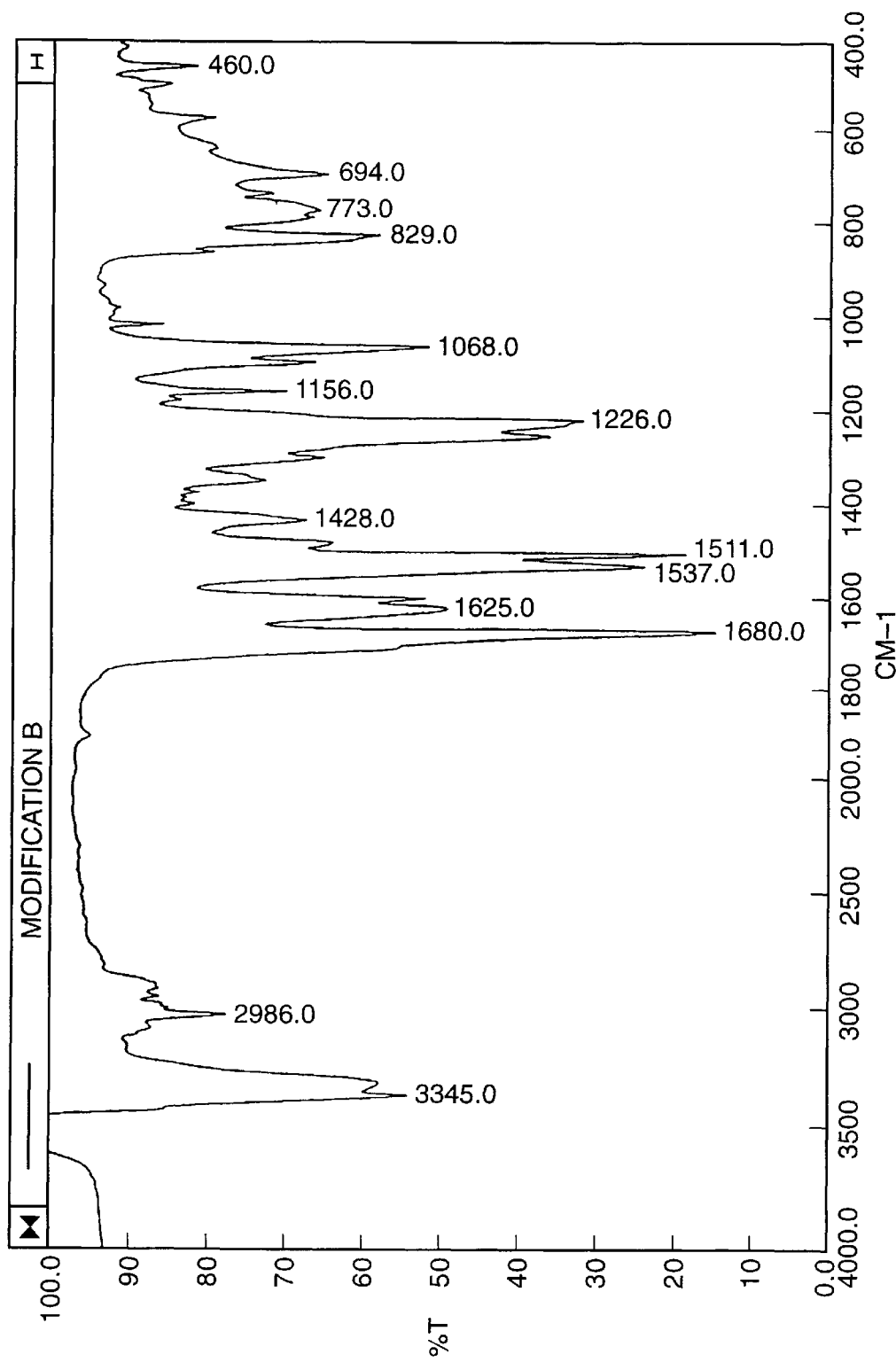

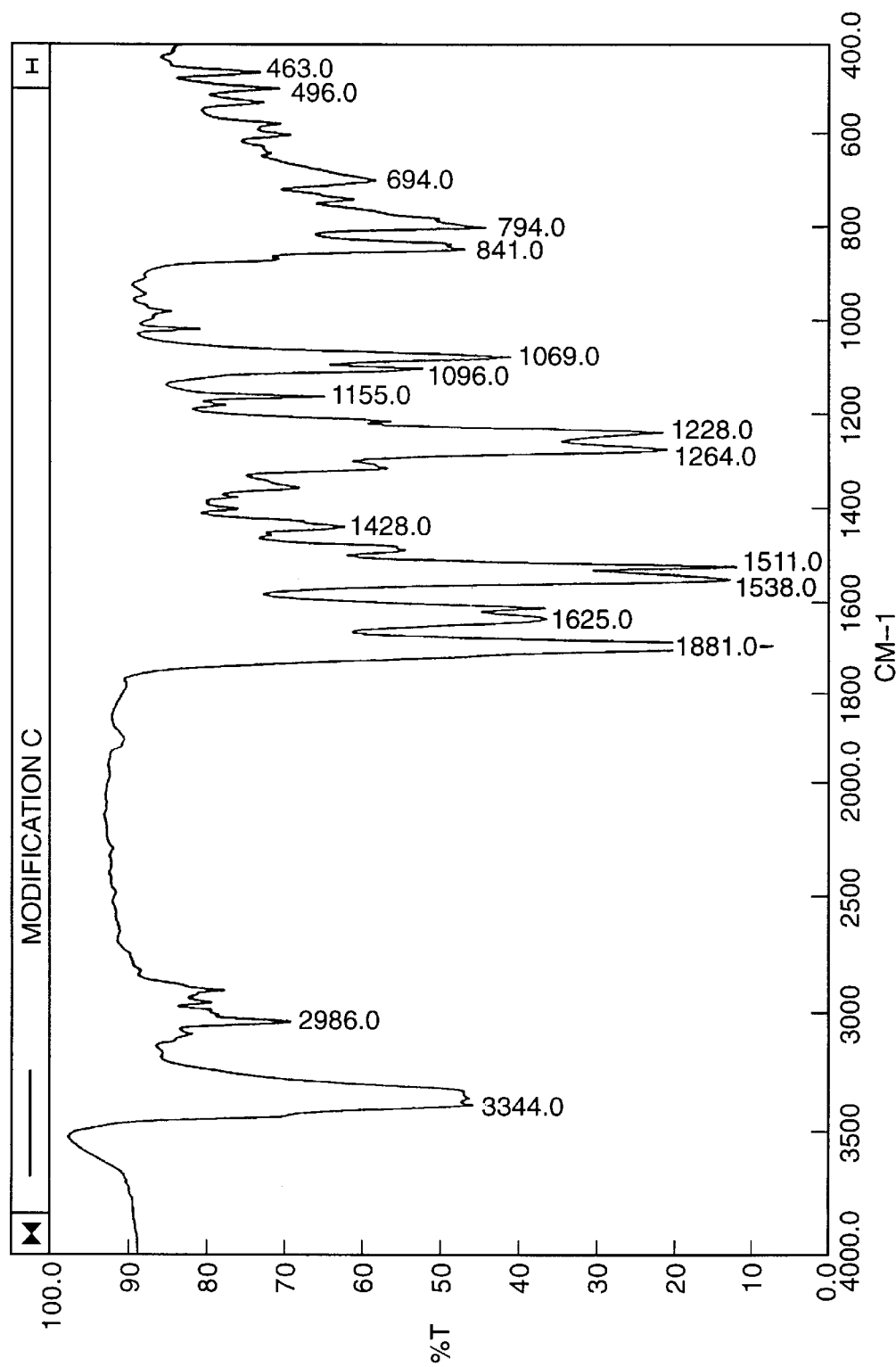

MODIFICATIONS OF 2-AMINO-4-(4-5FLUOROBENZYLAMINO)-1-ETHOXYCARBONYLAMINOBENZENE, AND PROCESSES FOR THEIR PREPARATION

BACKGROUND OF THE INVENTION

1. Field of the Invention

The invention relates to novel modifications of the compound 2-amino-4-(4-fluorobenzylamino)-1-ethoxycarbonylaminobenzene of the formula I

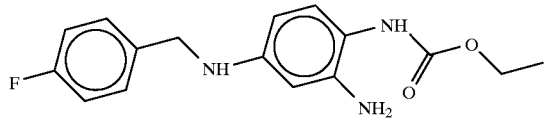

processes for their preparation and their use in pharmaceutical compositions.

2. Background Information

The compound of the formula I and it preparation is described in the patent DE 42 00 259.

This compound has, for example, anticonvulsive, antipyretic and analgesic activity and can thus be employed in pharmaceutical preparations.

In the crystallization of the compound of the formula I, however, in some cases very different mixed products are obtained with respect to the crystal size and form. Mixtures of crystal modifications are a great problem for pharmaceutical preparations. In particular, in the case of pharmaceutical forms having a high active compound content, physical inhomogeneties have a disadvantageous effect on adherence to constant pharmaceutical production conditions.

On the other hand, considerable variations in the stability, purity and uniformity of the finished product occur, so that the demands on the pharmaceutical quality of an active compound cannot be satisfied.

It is therefore of great interest to prepare the compound of the formula I in homogeneous crystalline form.

SUMMARY OF THE INVENTION

The invention is thus based on the object of preparing the compound of the formula I in homogeneous crystalline form which meets the pharmaceutical requirements.

It has now surprisingly been found that the compound of the formula I can be prepared in 3 different pure crystal modifications. Thus physically homogeneous compounds of the formula I can be prepared for the production of pharmaceutical finished products.

The 3 modifications, called A, B and C, have different physicochemical properties.

The in each case characteristic X-ray diffractograms are used for the identification of these three modifications of the compound of the formula I.

The modifications furthermore differ in their DSC curves (differential scanning calorimetry) and in some cases also in their IR spectra as well as by the crystal forms typical in each case.

BRIEF DESCRIPTION OF THE DRAWINGS

The X-ray diffractograms according to FIG. 1 were recorded with a powder diffractometer using $CuK_\alpha$ radiation.

The data for the DSC curve according to FIG. 2 relate to a heating rate of 10 k/min. The temperatures given in each case indicate the position of the intensity maximum.

Figure 1:
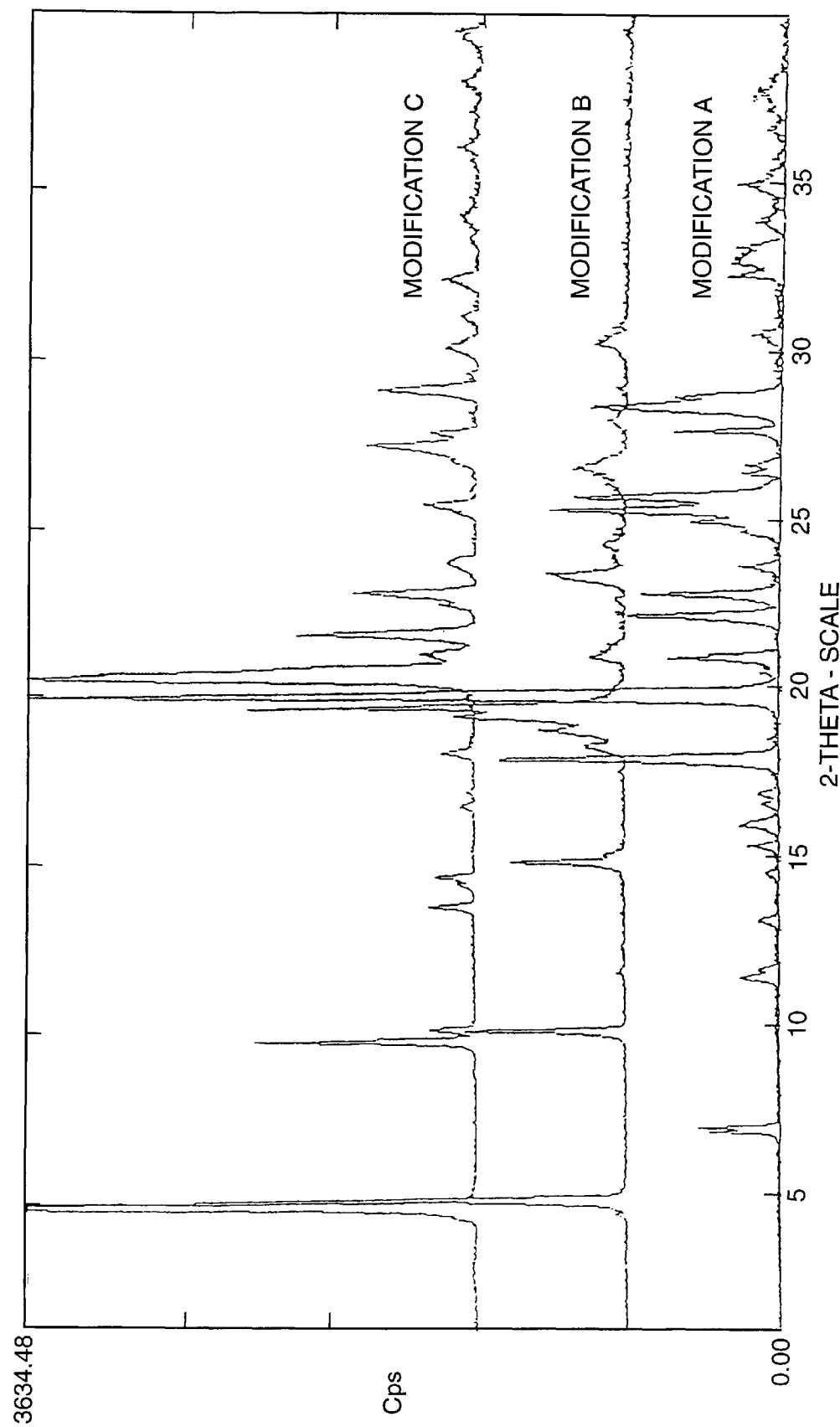
Figure 3A:
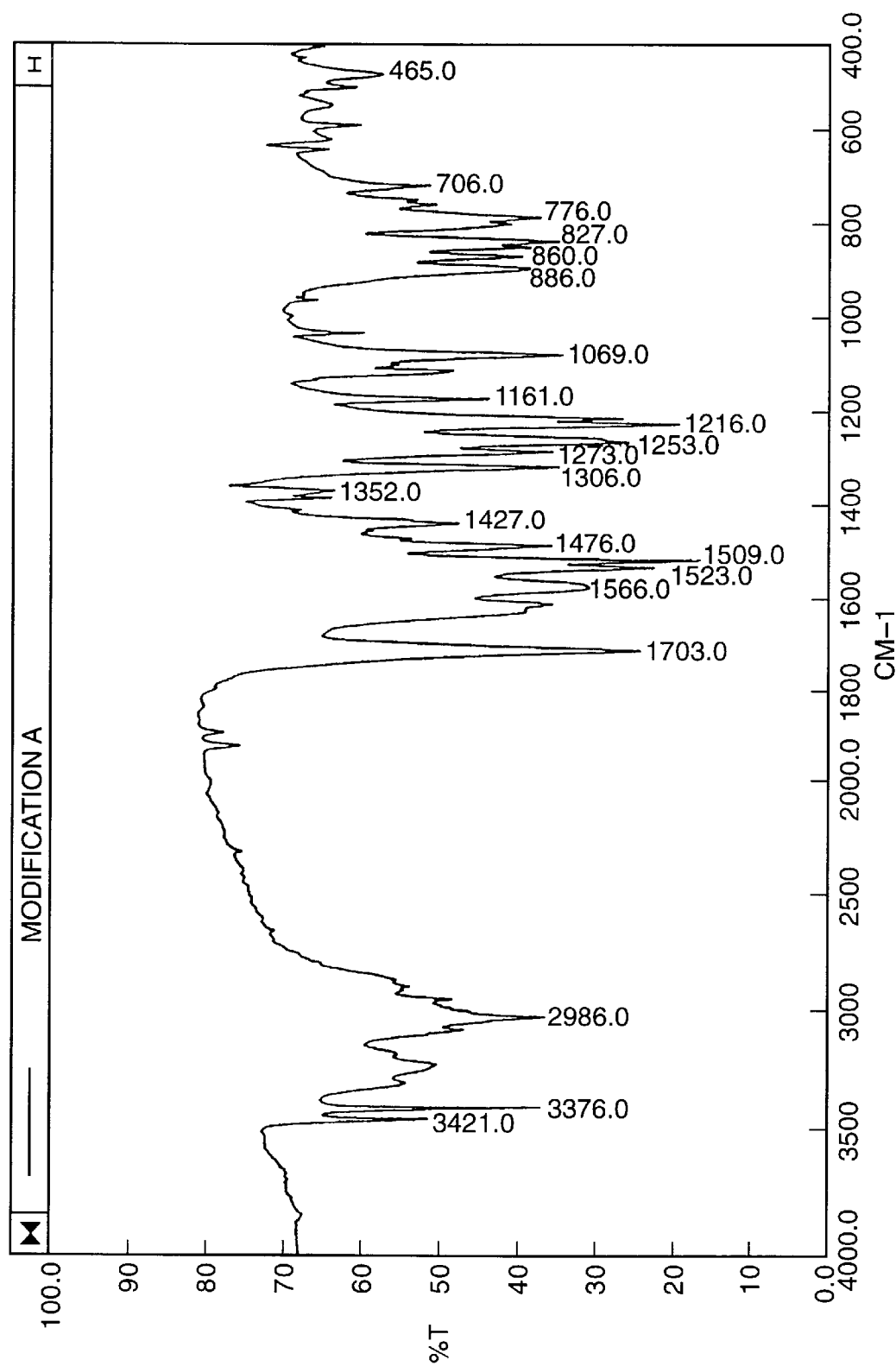

The IR spectra illustrated (FIG. 3a, b, c) were recorded on KBr pressed discs.

DETAILED DESCRIPTION OF THE INVENTION

The modification A is characterized by:

the X-ray diffractogram, reflections not coinciding with the reflections of the other two modifications being observed, inter alia, at 6.97°2 θ (12.67 Å), 18.02°2 θ (4.92 Å) and 19.94°2 θ (4.45 Å), the endothermic A, B conversion effect at approx. 97° C. (maximum) below the melting effect of the modification b at approx. 142° C. in the DSC curve, the IR spectrum differing from the other two modifications by intensive vibration bands at 3421 $cm^{-1}$ (ν N—H) 3376 $cm^{-1}$ (ν N—H), 1703 $cm^{-1}$ (ν C=O) and 886 $cm^{-1}$ (γ C—H), and mainly nearly isometric to short-columnar crystals.

The modification B is characterized by:

the X-ray diffractogram, reflections not coinciding with the reflections of the other two modifications being observed, inter alia, at 15.00°2 θ (5.90 Å), 19.29°2 θ (4.60 Å) and 19.58°2 θ (4.53 Å), the absence of thermal effects below the melting effect at approx. 142° C. in the DSC curve and mainly longish-tabular to columnar crystals.

The modification C is characterized by:

the X-ray diffractogram, reflections not coinciding with the reflections of the other two modifications being observed, inter alia, at 9.70°2 θ (9.11 Å) and 21.74°θ [sic] (4.09 Å), two endothermic effects connected with the phase transmission to the modification B between approx. 130° C. and the melting effect of the modification B at approx. 142° C. in the DSC curve and mainly tabular crystals.

The preparation of the 3 modifications of the compound I can be carried out by the following processes, adherence to the conditions being of particular importance.

The modifications can be prepared either from the crude product of the compound of the formula I or alternatively by modification conversion.

Preparation of the Modification A

The modification A can be prepared from the modifications B and C by stirring in solvents.

The crystallization of the modification A is preferably carried out with stirring of a supersaturated solution of the compound I in protic, dipolar-aprotic or non-polar solvents.

Protic solvents which can be employed are lower alcohols such as ethanol, 2-propanol, n-butanol, dipolar-aprotic solvents are acetonitrile or acetone and a non-polar solvent is toluene.

The crystallization is preferably carried out in the presence of lower alcohols.

The crystallization from the solution is carried in the temperature range from −20° C. to 110° C. In particular, in certain solvents, such as n-butanol, the crystallization of the pure modification A can be carried out at temperatures up to 110° C. The pure modification A is preferably obtained by crystallization in the temperature range from 20° C. to 50° C.

Preparation of the Modification B

The crystallization of the modification B is carried out from a saturated solution of the compound I with slow cooling.

The solvents employed can be protic solvents such as water or aprotic solvents such as toluene.

The crystallization is preferably carried out in the presence of toluene.

The crystallization from the solution can be carried out in the temperature range between 50° C. to and 110° C., but preferably between 80° C.–and 100° C.

The modification B can also be obtained by thermal phase conversion, preferably from the modification A at temperatures of greater than 80° C.

Preparation of the Modification C

The modification C crystallizes out at a temperature of 30° C.–80° C. with slow cooling from a saturated solution of the compound I in protic solvents such as ethanol and 2-propanol or aprotic solvents such as toluene.

The crystallization from the solution is preferably carried out at a temperature of 50° C.–70° C.

Each of these modifications of the compound I can be processed for administration in pharmaceutical forms which satisfy the pharmaceutical demands.

The present invention further relates to the use of the modifications A, B and C of the compound I for the production of pharmaceutical preparations. In particular, they are efficacious anti-epileptic agents and neuroprotective agents.

The pharmaceutical preparations can in general contain between 10 mg and 200 mg of at least one of the modifications of the compound I as an individual dose. Preferred administration forms are tablets.

The modifications of the compound of the formula I can be processed to give the pharmaceutical preparation in a customary manner using suitable exipients and/or auxiliaries.

The modification A of the compound I in particular shows advantageous properties for further pharmaceutical processing.

The crystal structure is stable up to approx. 80° C. Even after relatively long storage at temperatures up to 60° C. and relative atmospheric humidities up to 70%, no lattice changes are observed.

The modification A undergoes no lattice change on contact with solvents such as, for example, water, ethanol, acetone or toluene.

The nearly isometric to short-columnar crystal form leads to a grainy substance structure convenient for pharmaceutical processing.

The modifications B and C can be employed for specific pharmaceutical forms such as capsules and dry ampoules. Thus, for example, the preferred formation of finely granular and therefore particularly rapidly soluble crystals observed with the modification C can have advantages for the production of dry ampoules.

The preparation processes for the individual modifications will be illustrated in greater detail with the aid of examples:

EXAMPLE 1

Modification A 2.34 kg of the compound I and 0.16 kg of active carbon are dissolved by warming with stirring in 7.0 l of ethanol in a 16-l dissolving vessel. The solution is filtered hot through a pressure filter with stirring into a cooled 32-l crystallizing vessel with 0.5 l of ethanol such that the internal temperature in the crystallizing vessel is kept at <45° C. The remaining solution is then rinsed from the dissolving vessel through the pressure filter into the crystallizing vessel using 0.75 l of hot ethanol and the suspension is swiftly cooled. It is subsequently stirred at 5° C.–12° C. for 0.5 hours and the solid is filtered off with suction under inert conditions. The product is washed three times with 1.2 l of cooled ethanol each time. The crystallizate is then dried to weight constancy at 50° C.–55° C. in a vacuum drying oven. 2.04 kg (87% of theory) of the pure modification A is obtained.

EXAMPLE 2

Modification A 2 g of the modification C are stirred for 2 days at room temperature in 6 ml of ethanol. The modification A is obtained quantitatively.

EXAMPLE 3

Modification A 5 g of the modification B or C are stirred for 2 days at room temperature in 50 ml of toluene. The modification A is obtained quantitatively.

EXAMPLE 4

Modification A 3 g of the modification B are stirred for 2 days at room temperature in 1.5 ml of acetone. The modification A is obtained quantitatively.

EXAMPLE 5

Modification A 10 g of the compound I are dissolved in 5 ml of n-butanol with warming. The solution is allowed to crystallize at 105° C.–110° C., the mixture is cooled to 20° C. and the crystals are washed with n-butanol after filtering off with suction. The modification A is obtained quantitatively.

EXAMPLE 6

Modification B 10 g of the compound I are briefly heated to reflux with 20 ml of toluene and dissolved. The solution is allowed to crystallize at 90° C.–100° C. and the crystals are filtered off with suction and washed with 5 ml of toluene. After drying, 9.8 g (98% of theory) of needle-shaped crystals are obtained.

EXAMPLE 7

Modification B 10 g of substance of the modification A are kept for 8 hours at 100° C. in a drying oven. The modification B is obtained quantitatively.

EXAMPLE 8

Modification C 3.0 kg of the compound I are dissolved in a 32-l dissolving vessel by stirring with warming after addition of 0.2 kg of active carbon in 19.6 l of isopropanol. The solution is filtered hot through a pressure filter into a 32-l crystallizing vessel such that the internal temperature in the crystallizing vessel is kept at 60–65° C. The remaining solution is then rinsed from the dissolving vessel through the pressure filter into the crystallizing vessel using 2.5 l of hot isopropanol (about 70° C.). After the start of crystallization at 60° C.–65° C., the mixture is subsequently stirred. The suspension formed is swiftly cooled, subsequently stirred at 5° C.–12° C. and filtered off with suction under inert conditions. The crystallizate is washed three times with 2.5 l of cooled isopropanol each time.

The crystallizate is then dried to weight constancy in vacuo at 50° C.–55° C. 2.64 kg (88% of theory) of the active compound are obtained in modification C.

What is claimed is:

1. Process for the preparation of modification A of compound I

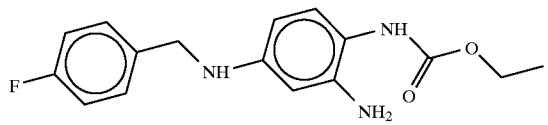

characterized by the X-ray diffractogram, reflections not coinciding with the reflections of the other two modifications being observed, inter alia, at 6.97°2 (12.67 Å), 18.02°2 (4.92 Å) and 19.94°2 (4.45 Å);

wherein the pure crystal form is allowed to crystallize out of a supersaturated solution of the compound I in protic, dipolar-aprotic or non-polar solvent.

2. Process for the preparation of modification A of compound I

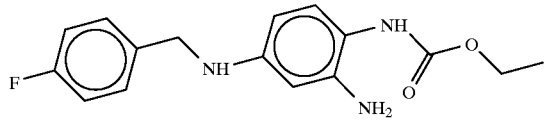

characterized by the X-ray diffractogram, reflections not coinciding with the reflections of the other two modifications being observed, inter alia, at 6.97°2 (12.67 Å), 18.02°2 (4.92 Å) and 19.94°2 (4.45 Å);

wherein the substances of the modifications B and C are treated with protic, dipolar-aprotic or non-polar solvents at low temperature.

3. The process of claim 2, wherein the substances of the modifications B and C are treated with protic, dipolar-aprotic or non-polar solvents at room temperature.

4. Process for the preparation of modification B of compound I

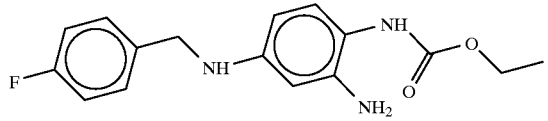

characterized by the X-ray diffractogram, reflections not coinciding with the reflections of the other two modifications being observed, inter alia, at 15.00°2 (5.90 Å), 19.29°2 (4.60 Å) and 19.58°2 (4.53 Å);

wherein the pure crystal form is allowed to crystallize out at a temperature of greater than 80° C. from a saturated solution of the compound I in protic or non-polar solvents.

5. Process for the preparation of modification B of compound I

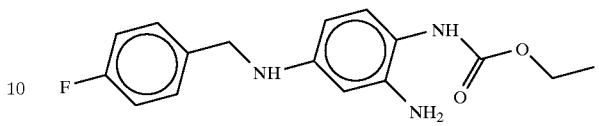

characterized by the X-ray diffractogram, reflections not coinciding with the reflections of the other two modifications being observed, inter alia, at 15.00°2 (5.90 Å), 19.29°2 (4.60 Å) and 19.58°2 (4.53 Å);

wherein modification B is prepared from modification A at temperatures of greater than 80° C. by thermal phase conversion.

6. Process for the preparation of modification C of compound I

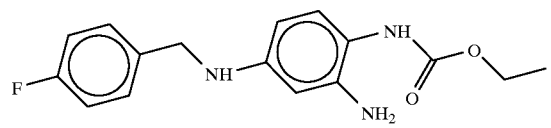

characterized by the X-ray diffractogram, reflections not coinciding with the reflections of the other two modifications being observed, inter alia, at 9.70°2 (9.11 Å) and 21.74°2 (4.09 Å);

wherein the pure crystal form is allowed to crystallize out at a temperature of from 50° C. to 70° C. from a saturated solution of compound I in protic or non-polar solvents.

7. Process for the preparation of modification C according to claim 6, wherein the solvent is selected from the group consisting of ethanol, 2-propanol and toluene.

8. Process for the preparation of the modification A according to claim 1, characterized in that the crystallization from the solution is carried out at temperatures from –20° C. to 110° C., preferably at 20° C. to 50° C.

9. Process for the preparation of the modification A according to claim 7 or claim 8 characterized in that protic solvents which can be employed are lower alcohols such as ethanol, 2-propanol or n-butanol, dipolar-aprotic solvents are acetonitrile or acetone and the non-polar solvent is toluene.

10. Process according to claim 9, characterized in that lower alcohols are preferably used as solvents.

11. Process for the preparation of the modification B according to claim 4, characterized in that the protic solvent preferably employed is water and the non-polar solvent is toluene.

12. Process for the preparation of the modification C according to claim 6, characterized in that the crystallization from the solution is carried out at temperatures from 60° C. to 70° C.

* * * * *

UNITED STATES PATENT AND TRADEMARK OFFICE
CERTIFICATE OF CORRECTION

PATENT NO. : 5,914,425
DATED : June 22, 1999
INVENTOR(S) : Meisel et al.

It is certified that error appears in the above-identified patent and that said Letters Patent is hereby corrected as shown below:

Title page,
Item [54], Title, replace "5FLUOROBENZYLAMINO" with
-- FLUOROBENZYLAMINO --.

Column 6,
Line 46, replace "7" with -- 1 --.

Signed and Sealed this

Sixth Day of September, 2005

JON W. DUDAS
*Director of the United States Patent and Trademark Office*